US007365852B2

(12) United States Patent
Schleifer (10) Patent No.: US 7,365,852 B2
(45) Date of Patent: Apr. 29, 2008

(54) METHODS AND SYSTEMS FOR SELECTING PATHLENGTH IN ABSORBANCE MEASUREMENTS

(75) Inventor: Arthur Schleifer, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 337 days.

(21) Appl. No.: 10/996,913

(22) Filed: Nov. 24, 2004

(65) Prior Publication Data

US 2006/0109469 A1    May 25, 2006

(51) Int. Cl.
*G01N 21/00* (2006.01)

(52) U.S. Cl. .................. 356/440; 356/441; 356/442

(58) Field of Classification Search ................ 356/436, 356/440, 441, 442, 413
See application file for complete search history.

(56) References Cited

U.S. PATENT DOCUMENTS

| 4,786,171 | A | * | 11/1988 | LeFebre et al. | ............. 356/326 |
| 4,981,362 | A | * | 1/1991 | deJong et al. | ............. 356/436 |
| 6,628,382 | B2 | * | 9/2003 | Robertson | .................... 356/246 |
| 2002/0140931 | A1 | | 10/2002 | Robertson | |
| 2006/0077390 | A1 | * | 4/2006 | Kralik | ........................ 356/427 |

* cited by examiner

*Primary Examiner*—Layla G. Lauchman
*Assistant Examiner*—Scott M Richey (57) ABSTRACT

Methods and sub-systems for substantially optimizing the absorbance measurement in optical instruments are provided. A method comprises forming a liquid sample into a droplet extending between two opposing surfaces, passing a light beam through the sample, and varying the distance between the two opposing surfaces until a distance substantially corresponding to a optimum absorbance is obtained.

14 Claims, 5 Drawing Sheets

METHODS AND SYSTEMS FOR SELECTING PATHLENGTH IN ABSORBANCE MEASUREMENTS

BACKGROUND OF THE INVENTION

There are many use environments, the fields of medical research and pharmaceutical development being examples, where it is necessary to accurately acquire fluid samples with volumes which may be as small as a few nanoliters. In these same fields, it is also often desirable to measure optical characteristics of the acquired fluid samples. Such optical characteristics include, for example, the ability of a sample to absorb light.

For instance, UV-Visible Spectrophotometry may be used to characterize the chemical composition of a liquid sample (in solution or suspension phase) using the absorbed spectra of the sample. The light absorbance of a sample depends on the pathlength L of light passing through the sample, as well as on the concentration of light absorbers (e.g., biomolecules, cells, etc) in a sample solution and the wavelength ($\lambda$) of light being used to characterize the sample. The wavelengths of UV-Visible light span from 200 nm to 800 nm, while ultraviolet wavelengths range from 200 to 400 nm.

UV-Visible spectrophotometry provides a way to determine the concentration, purity, and integrity of a biological sample without requiring additional sample preparation other than acquiring a sample. UV-Visible Spectrophotometry measurements depend on the light source (UV lamp), the sample and sampling technique. Most biological samples absorb electromagnetic radiation at wavelengths ranging from 200 nm to 800 nm, mostly 230, 260 and 280 nm. For a DNA or RNA sample in aqueous phase, one unit of absorbance 1 Å measured at a $\lambda$ 260 nm and a pathlength of 10 mm is equal to 50/(40) ng/$\mu$l Most biological samples are highly concentrated for down-stream process purpose (such as microarray spotting or protein sample preparation for mass spectrometer). The absorbance of such samples can be above the saturation limit for typical spectrophotometers if the pathlength is about 10 mm. While the sample concentration range can be extended by diluting the sample, diluting sample requires additional laboratory work and can result in errors.

Absorbance measurements on instruments, such as spectrophotometers, have a useful range where the measurement errors are minimal. As the absorbance approaches zero or the lower absorbance limit of the instrument (maximum transmittance), the uncertainties in the absorbance measurement are dominated by noise. It is difficult to measure a small change within a large signal. As the absorbance approaches infinity or the higher absorbance limit of the instrument (zero transmittance), the resulting signal has a lower amplitude than practical for measurement. In addition to the random errors inherent in measuring very low signals, stray light that reaches the detector of the instrument, limits the ability of a spectophotometer to measure at high absorbance, so that at a high concentration of sample, the absorbance measurement is lower than predicted.

Some conventional cuvetteless spectrophotometers can be used to measure the absorbance of small volume liquid samples (e.g., between 1-2 $\mu$l). These instruments typically provide a sample stage on which a sample droplet may be placed and an opposing surface which can be brought into contact with the droplet. By increasing the distance between the two surfaces, the droplet is stretched. Both the sample stage and the opposing surface are in communication with the respective ends of a source-side and detection-side optical fiber. Light from a light source passes through the source side optical fiber through the sample droplet to the detection-side fiber and is received by a detector within the instrument, permitting absorbance measurements of the sample.

However such instruments do not provide the capability for optimizing the absorbance measurement.

BRIEF SUMMARY OF THE INVENTION

In one embodiment, the invention provides a method of measuring an optical property of a sample. In one aspect, the method comprises placing at least a portion of a liquid sample on at least one of two opposing surfaces, contacting the liquid sample placed on one surface with the other opposing surface, and varying the distance between the two opposing surfaces until a predetermined distance substantially corresponding to a substantially optimum absorbance is obtained.

In one embodiment, the system of this invention includes a source of electromagnetic radiation, a first optical sub-system, a sample holding assembly having two opposing surfaces capable of being spaced apart from each other, a second optical sub-system, a detecting sub-system for detecting electromagnetic radiation, a positioning sub-system for varying a distance between the two opposing surfaces, and a processing sub-system. The first optical sub-system can provide electromagnetic radiation from the source to the sample holding assembly. The sample holding assembly can place the liquid sample in an optical path of the provided electromagnetic radiation. The provided electromagnetic radiation is also transmitted through at least a portion of the sample holding assembly. The second optical sub-system can receive electromagnetic radiation transmitted through the sample and at least a portion of the sample holding assembly and can also transmit the received electromagnetic radiation to the detecting sub-system. The processing sub-system includes a data collector interface component operatively connected to the detector and capable of receiving detected data, one or more processors, a positioning sub-system interface component capable of providing positioning information to the positioning sub-system, and, one or more computer readable memories having computer readable code embodied therein, the computer readable code capable of causing the one or more processors to:

receive the detected data,
vary the distance between the two opposing surfaces until a distance within a substantially optimum absorbance range (also referred to as a distance corresponding substantially to a substantially optimum absorbance) is obtained.

BRIEF DESCRIPTION OF THE SEVERAL VIEWS OF THE DRAWING

For a better understanding of the present invention, together with other and further needs thereof, reference is made to the accompanying drawings and detailed description and its scope will be pointed out in the appended claims.

DETAILED DESCRIPTION OF THE INVENTION

Methods and system for substantially optimizing the absorbance measurement in optical instruments are disclosed hereinbelow.

Figure 1A:
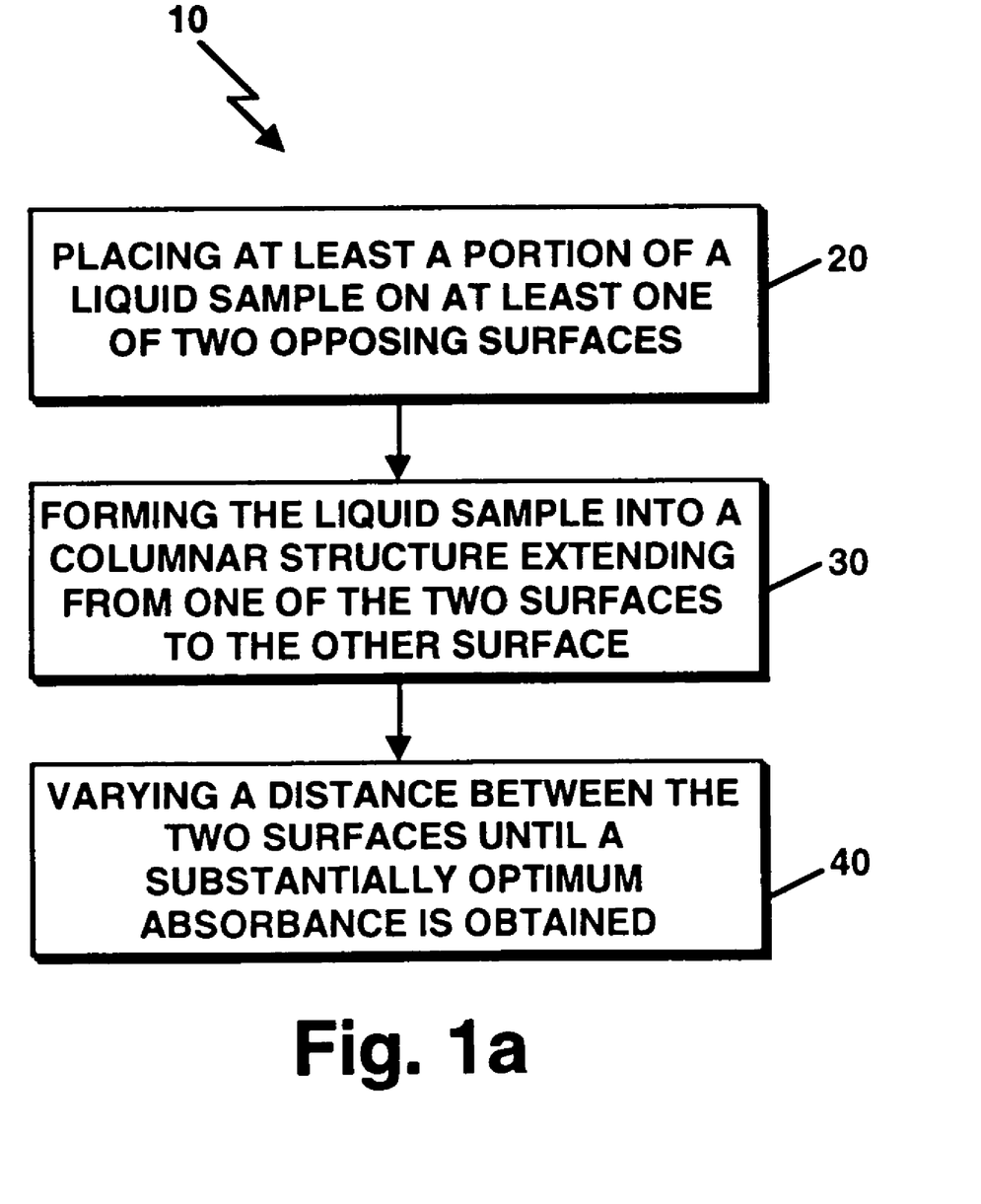
FIGS. 1a and 1b are schematic flowchart diagram representation of an embodiment of the method of this invention.

A flowchart diagram representation of an embodiment of the method of this invention is shown in FIG. 1a. Referring to FIG. 1a, the embodiment of the method of this invention shown therein includes, the steps of placing at least a portion of a liquid sample on at least one of two opposing surfaces (step 20, FIG. 1a), contacting the sample placed on one surface with the other opposing surface, forming the liquid sample into a droplet that extends from one of the two opposing surfaces to another one of the two opposing surfaces (a columnar structure in one instance) (step 30, FIG. 1a), and varying a distance between the two opposing surfaces until a distance within a substantially optimum absorbance range (also referred to as a distance substantially corresponding to a substantially optimum absorbance, and, in one embodiment, predetermined) is obtained (step 40, FIG. 1a).

Figure 1B:
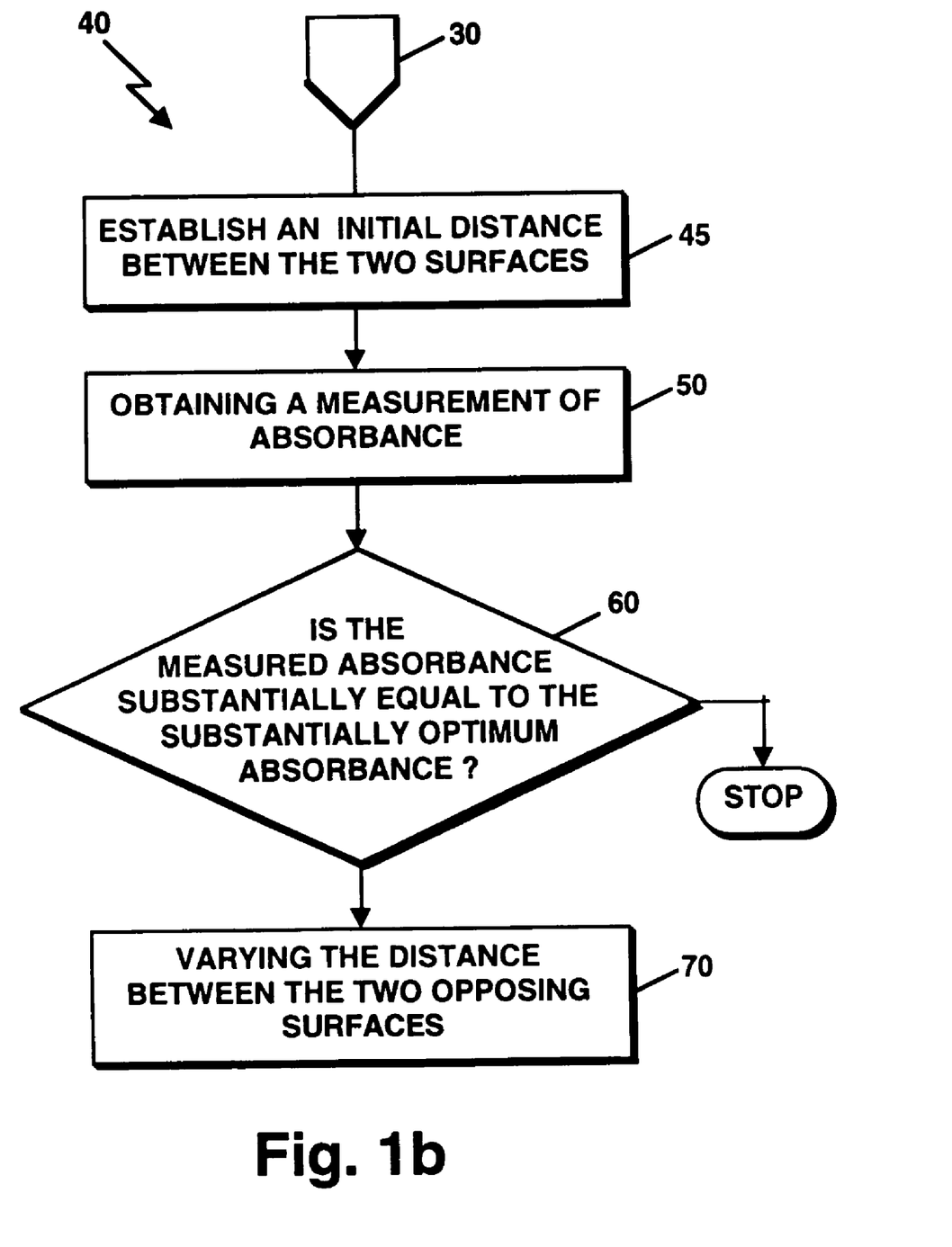

An embodiment of the step (step 40, FIG. 1a) of varying the distance between the two opposing surfaces is shown in FIG. 1b. Referring to FIG. 1b, the embodiment of the step (step 40, FIG. 1a) of varying the distance between the two opposing surfaces includes (a) establishing an initial distance between the two surfaces, (b) obtaining a measurement of absorbance, (c) determining whether the measured absorbance is substantially equal to the substantially optimum absorbance, (d) further varying the distance between the two opposing surfaces, if the measured absorbance is not substantially equal to the substantially optimum absorbance, and (e) repeating steps (b) through (d) until the measured absorbance is substantially equal to the substantially optimum absorbance.

In one embodiment, the substantially optimum absorbance range of values can be obtained by initial measurement or calibration, or dynamically. For some embodiments of optical instruments, spectrophotometers, the value of the substantially optimum absorbance is 0.4, although that value is not a limitation of this invention. In another embodiment, the value of the substantially optimum absorbance can be obtained dynamically through iteration during the measurement process disclosed above and in FIG. 1b.

The substantially optimum absorbance range results from the properties of the measurement instrument. All measurement instruments have sources of noise, such as, but not limited to, electronic noise, stray light effects. In an optical instrument measuring absorption, such as, but not limited to, a spectrophotometer, the noise has effect on both high and low absorption samples. In addition to noise, instruments also exhibit saturation effects at high signal levels. For optical instruments measuring absorption, such as, but not limited to, spectrophotometers, the resulting measurement is absorbance and the desired result is concentration or presence of an analyte. The light transmittance T is defined as $$T(\lambda) = I/I_0 \quad (1)$$

where I is the light intensity after traveling through sample, $I_0$ (also referred to as the reference intensity) is the intensity obtained after traveling through a blank sample (host liquid or solvent). $\lambda$ is the wavelength of light ("light" is used herein to refer to electromagnetic radiation). The absorbance A is defined as:

$$A = -\log(T) \quad (2)$$

For high absorption, the transmitted intensity, I, is small and noise can have the appearance of desired signal. For a large transmitted intensity, the measured intensity, I, has a value that is approximately the same as the reference intensity, $I_o$, and noise can mask the final desired result, The substantially optimum absorbance range can be determined when the instrument is characterized or from the characterization of instrument noise and saturation. The substantially optimum absorbance range is a range of values, located between the smallest transmitted intensity and the saturation transmitted intensity, at which signal to noise ratio is substantially optimum or maximized.

Figure 2:
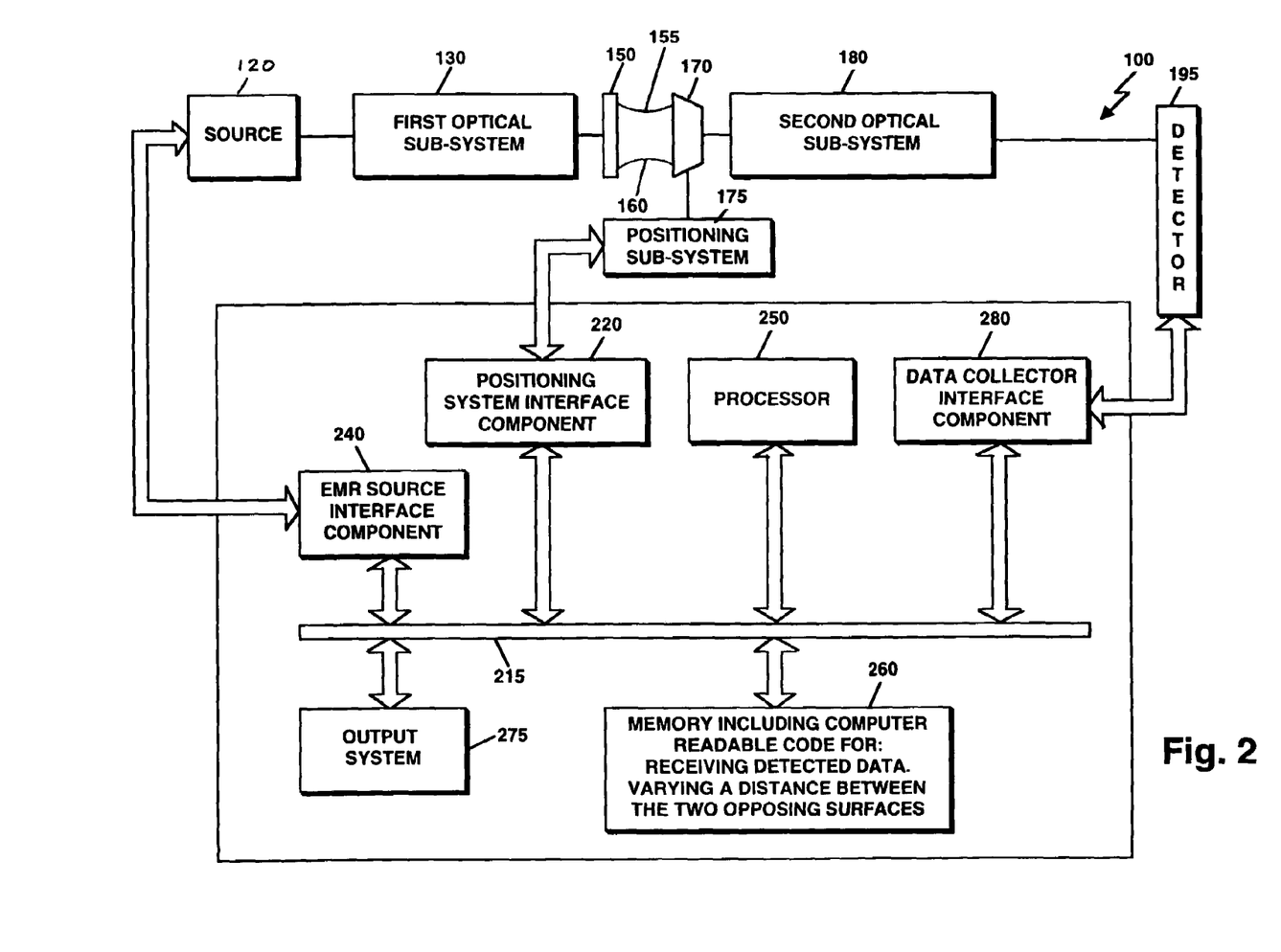
FIG. 2 is a schematic block diagram representation of an embodiment of the system of this invention.

A block diagram representation of an embodiment 100 of the system of this invention is shown in FIG. 2. Referring to FIG. 2, the embodiment 100 shown therein includes a source 120 of electromagnetic radiation, a first optical sub-system 130, and a sample holding assembly 170 having two opposing surfaces 150, 160, where the sample holding assembly 170 is capable of confining a liquid sample 155 between the surfaces 150, 160 and by the surface tension of the liquid sample 155. The first optical sub-system 130 is capable of providing electromagnetic radiation from the source 120 to the sample holding assembly 170. The sample holding assembly 170 is capable of placing the liquid sample 155 in an optical path of the provided electromagnetic radiation. The provided electromagnetic radiation is also transmitted through at least a portion of the sample holding assembly 170. The embodiment 100 shown in FIG. 2 also includes a second optical sub-system 180, a detecting sub-system 195 capable of detecting electromagnetic radiation, a positioning sub-system 175 capable of varying a distance between the two opposing surfaces 150, 160, a data collector interface component 280 operatively connected to the detector 195 and capable of receiving detected data, one or more processors 250, a positioning sub-system interface component 220 capable of providing positioning information to the positioning sub-system 175, and, one or more computer readable memories 260 (also referred to as computer usable media) having computer readable code embodied therein. The second optical sub-system 180 is capable of receiving electromagnetic radiation transmitted through the sample 155 and at least a portion of the sample holding assembly 170 and is also capable of transmitting the received electromagnetic radiation to the detecting sub-system 195. The detecting sub-system 195 is optically disposed to receive electromagnetic radiation from the second optical sub-system 180. The computer readable code is capable of causing the one or more processors 250 to:

receive detected data from the detector 195, and vary a distance between the two opposing surfaces 150, 160 until a predetermined distance corresponding to a substantially optimum absorbance is obtained.

Optionally, the computer readable code can be used to determine a substantially optimal absorbance measurement from a sample. In one aspect, the substantially optimal absorbance measurement is determined after a plurality of optical absorbance measurements are provided to the data collector interface component 280.

The data collector interface component 280, the one or more processors 250, the positioning sub-system interface component 220 and the one or more computer readable memories 260 are operatively interconnected through interconnection means 215 (such as, but not limited to, a common "bus").

In one embodiment, the system of this invention includes an electromagnetic radiation source interface component 240 capable of providing a control signal to the source 120 of electromagnetic radiation. The electromagnetic radiation source interface component 240 is operatively interconnected with the one or more processors 250, the positioning sub-system interface component 220 and the one or more computer readable memories 260.

In another embodiment of the system of this invention including an electromagnetic radiation source interface component 240, the computer readable code is also capable of causing the one or more processors 250 to obtain an initial absorbance measurement. Such an embodiment enables, if the relationship between distance and absorbance is known, the determination of a desired distance between the two opposing surfaces 150, 160 and the setting of substantially such a desired distance between the two opposing surfaces 150, 160.

In a further embodiment of the system of this invention including an electromagnetic radiation source interface component 240, the computer readable code is also capable of causing the one or more processors 250 to:

(a) obtain a measurement of absorbance;
(b) determine whether the measured absorbance is substantially equal to the substantially optimum absorbance;
(c) vary the distance between the two opposing surfaces 150, 160, if the measured absorbance is not substantially equal to the substantially optimum absorbance;
(d) repeat steps (a) through (c) until the measured absorbance is substantially equal to the substantially optimum absorbance.

This embodiment allows the distance between the two opposing surfaces 150, 160 (path length) to be varied substantially continuously or step-wise. Once the liquid sample 155 is in contact with the two opposing surfaces 150, 160, the distance is either increased or decreased until the substantially optimum absorbance signal is measured. In one embodiment, the substantially optimum absorbance signal about 0.4 absorbance units.

During operation of one embodiment of the system of this invention, samples are loaded onto the first surface 150 with a pipetting means. The droplet when emptied from the pipette, if of sufficient volume, will spread to cover at least a portion of the lower surface 150. The second surface 160 is brought into close proximity to the lower surface 150, making contact with the deposited droplet wetting the entire confining surface before extending the droplet 155 between the two surfaces 150 and 160. In one aspect, the extended droplet has a substantially columnar shape. The liquid sample 155 is contained by its surface tension between surfaces 150 and 160.

By applying blank samples (samples containing the diluting liquid but not the analyte of interest) the difference in transmitted light intensity can be used to characterize the sample according to $A = -\log(I/I_0)$, where $I_0$ is level of transmitted light with the component being analyzed absent, and I is the level of light transmitted through the sample and A is the absorbance value which can be related to the concentration of the component being analyzed by Beer's law. (Beer's Law expresses the absorbance in terms of sample concentration, c, or more precisely, the optical density or number density of the sample, and the optical path length, L, as $$A(\lambda,L) = -\log T(\lambda) = 0.434\sigma(\lambda)cL$$

where $\sigma(\lambda)$ is dependent on the sample molecule structure and wavelength.)

In another embodiment of the operation, samples are loaded in two parts, one onto each of the opposing surfaces 150, 160.

In one embodiment, one of the two opposing surfaces 150, 160 can include the end of an industry standard SMA fiber optic connector.

In another embodiment, one of the two opposing surfaces 150, 160 can include, but is not limited to, an assembly which has one or more of the following features: UV/visible transparent, abrasion-resistant, a optical-quality hydrophilic center (comprised of a material such as, but not limited to, Quartz glass or Polystyrene. The transmittance of the sample holding assembly 170 is selected to ensure that a measured signal remains within the limit of the linear absorbance range of the system. In one aspect, at least one of the surfaces 150, 160 of the holding assembly 170 includes an abrasion-resistant hydrophobic surround (comprised of a material such as, but not limited to, Silicone, Fluorosilicone, Fluorosilane, Teflon® (polytetrafluoroethylene) emulsion or Teflon® AF). In one aspect, the sample (e.g., a drop) is placed on a transparent center of at least one of the surfaces 150, 160.

The source 120 of electromagnetic radiation can be, but is not limited to, a UV/visible LED light source, a Xenon flash lamp, or a Deuterium lamp for UV and a tungsten source for visible.

In one embodiment, each of the surfaces 150, 160 is attached by means of mounting components to a stage-like component having at least one movable section, the at least one movable section being capable of being moved by the positioning sub-system 175. Such positioning sub-system 175 can include electrical motors (for example, but not limited to, stepper motors, DC motors, linear motors; the motors can be direct drive or the positioning sub-system can include coupling mechanisms to translate the motor motion to relative motion of the surfaces 150, 160.

In one embodiment, the first optical sub-system 130 comprises an optical fiber sub-system directly connected between the source 120 and the surface 150 and the second optical sub-system 180 comprises another optical fiber sub-system directly connected to other surface 160.

Figure 3:
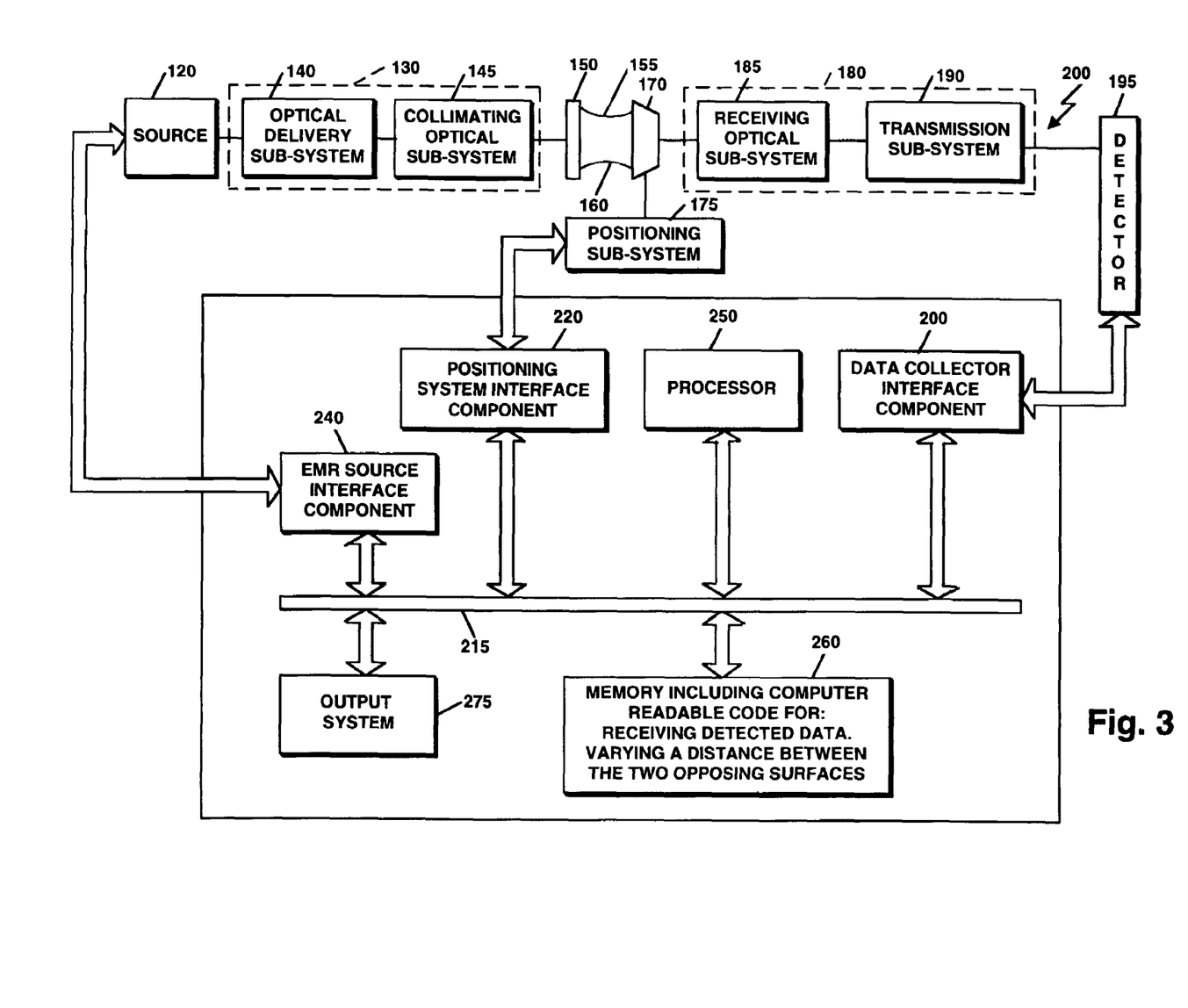
FIG. 3 is a schematic block diagram representation of another embodiment of the system of this invention.

In another embodiment 200, shown in FIG. 3, the first optical sub-system 130 comprises a collimating optical sub-system 145 and an optical delivery sub-system 140 capable of providing electromagnetic radiation from the source 120 to the collimating optical sub-system 145; and, the second optical sub-system 180 comprises a receiving optical sub-system 185 capable of receiving electromagnetic radiation transmitted through the sample and at least a portion of the sample holding assembly 170, and, an optical transmission sub-system 190 capable of receiving electromagnetic radiation from the receiving optical sub-system 185 and transmitting the received electromagnetic radiation to the detecting sub-system 190. The collimating optical sub-system 145 is capable of substantially collimating the electromagnetic radiation provided to one surface 150 of the sample holding assembly 170.

The collimating optical sub-system 145 can be, but is not limited to, a plano-convex lens that collimates electromagnetic radiation and directs it towards one surface 150 of the sample holding assembly 170 or an optical sub-system to perform the same function. In some embodiments, the collimating optical sub-system 145 can include optical components, such as, but not limited to, prisms or reflecting components that redirect the collimated electromagnetic radiation.

Figure 4:
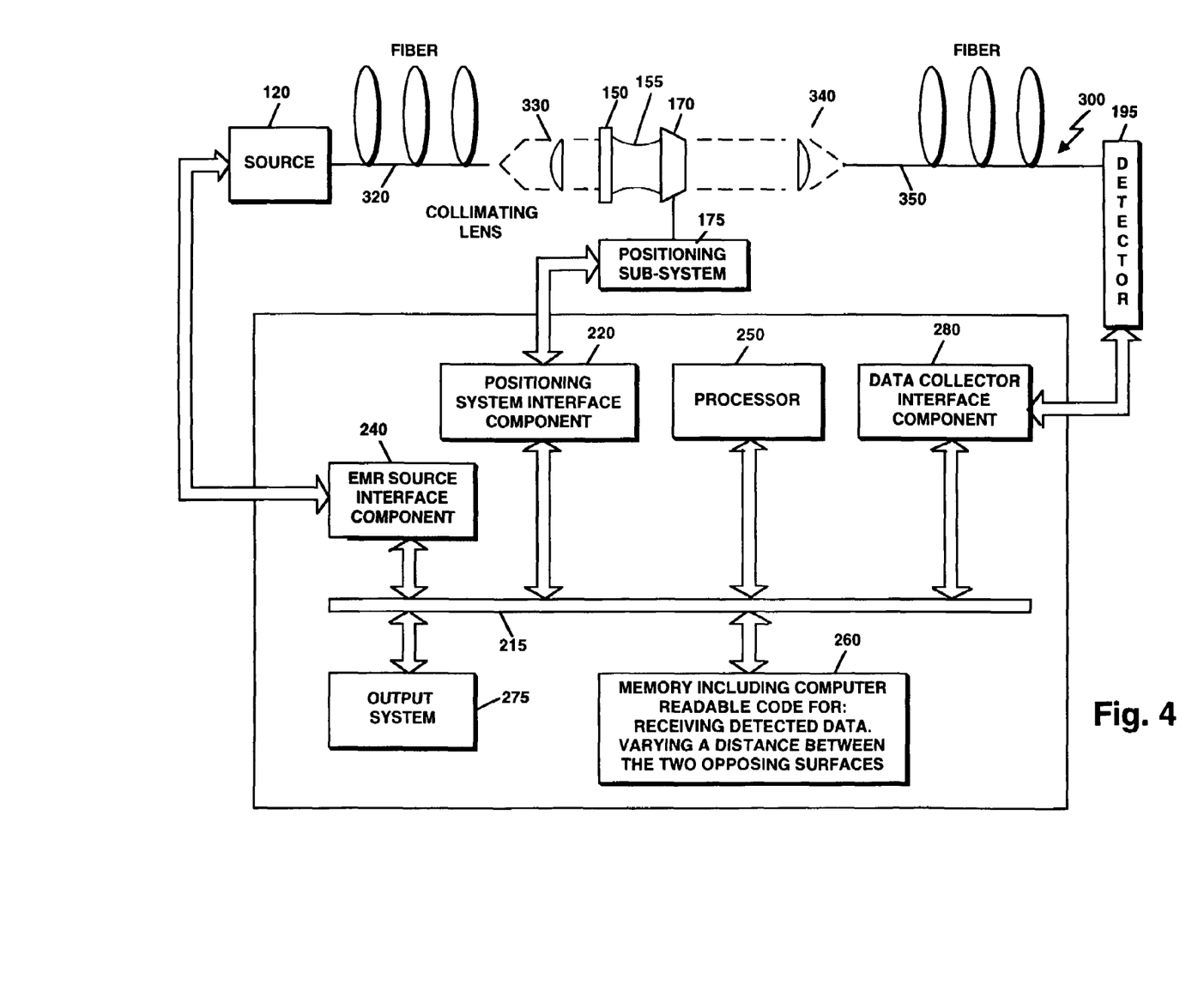
FIG. 4 is a schematic block diagram representation of yet another embodiment of the system of this invention.

The receiving optical sub-system 185 can be, but is not limited to, a lens that receives the electromagnetic radiation transmitted through the sample 155 and at least a portion of the sample holding assembly 170 and couples the received electromagnetic radiation onto the optical transmission sub-system 190. The optical transmission sub-system 190, capable of receiving electromagnetic radiation from the receiving optical sub-system 185 and transmitting the received electromagnetic radiation to the detecting sub-system 195, can include, but is not limited to, a fiber optic path and optical components to image the transmitted electromagnetic radiation onto the detecting sub-system 195 (as shown in FIG. 4), or, in another embodiment, an optical sub-system including discrete optical components for receiving/transmitting the electromagnetic radiation and imaging the transmitted electromagnetic radiation onto the detecting sub-system 195. The detecting sub-system 195 can include, but is not limited to, photodiodes (one or more), diode array detectors and, depending on the desired measurement, photovoltaic (such as photodiodes), photoconductive or photoemissive detectors.

In another detailed embodiment 300, shown in FIG. 4, the optical delivery sub-system (140, FIG. 2) comprises a first optical fiber 320 (including any optical components necessary to focus the electromagnetic radiation from the source 120 onto the fiber 320), the collimating optical sub-system (145, FIG. 2) comprises a plano-convex lens 330 that collimates the electromagnetic radiation emanating from the fiber 320), the optical transmission sub-system (190, FIG. 2) comprises a second optical fiber 350 and optical components to image the transmitted electromagnetic radiation onto the detecting sub-system 195, and the receiving optical sub-system (185, FIG. 2) can be, but is not limited to, a lens 340 that receives the electromagnetic radiation transmitted through the sample 155 and at least a portion of the sample holding assembly 170 and couples the received electromagnetic radiation onto the second optical fiber 350.

In a further embodiment (not shown) of the system of this invention, the first optical sub-system 130 comprises a first optical fiber (including any optical components necessary to focus the electromagnetic radiation from the source 120 onto the first optical fiber) and the second optical sub-system 180 comprises a second optical fiber and optical components to image the transmitted electromagnetic radiation onto the detecting sub-system 195.

In general, the techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to data entered using the input device to perform the functions described and to generate output information. The output information may be applied to one or more output devices.

Elements and components described herein may be further divided into additional components or joined together to form fewer components for performing the same functions.

Each computer program (code) within the scope of the claims below may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable or usable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge, a carrier wave, or any other medium from which a computer can read.

Although the invention has been described with respect to various embodiments, it should be realized this invention is also capable of a wide variety of further and other embodiments within the spirit and scope of the appended claims.

What is claimed is:

1. A method for optimizing measurement of small liquid sample volumes, the method comprising:
   placing at least a portion of a liquid sample on at least one of two opposing surfaces;
   forming the liquid sample into a droplet extending from one of the two opposing surfaces to another one of the two opposing surfaces at an initial distance between the two surfaces;
   obtaining an initial absorbance measurement and determining whether the initial absorbance measurement is the substantially optimum absorbance; wherein the substantially optimum absorbance is a measured absorbance at which the signal-to-noise ratio is maximized; and
   if the initial absorbance measurement is not the substantially optimum absorbance, varying a distance between the two opposing surfaces until a distance is obtained that provides a substantially optimum absorbance.

2. The method of claim 1 wherein the step of varying the distance between the two opposing surfaces comprises:
   (a) obtaining a measurement of absorbance;
   (b) determining whether the measured absorbance is substantially equal to the substantially optimum absorbance;
   (c) further varying the distance between the two opposing surfaces, if the measured absorbance is not substantially equal to the substantially optimum absorbance;
   (d) repeating acts (a) through (c) if the measured absorbance is not substantially equal to the substantially optimum absorbance.

3. A system comprising:
   a source of electromagnetic radiation;
   a first optical sub-system:
   a sample holding assembly comprising two opposing surfaces spaced apart from each other and arranged to hold a liquid sample;
   said first optical sub-system arranged to provide electromagnetic radiation from said source to said sample holding assembly;

said sample holding assembly arranged to place the liquid sample in an optical path of the provided electromagnetic radiation; the provided electromagnetic radiation also being transmitted through at least a portion of said sample holding assembly;

a second optical sub-system; said second optical sub-system arranged to receive electromagnetic radiation transmitted through the sample and said at least a portion of said sample holding assembly;

a detecting sub-system arranged to detect electromagnetic radiation;

said second optical sub-system arranged to transmit the received electromagnetic radiation to said detecting sub-system;

said detecting sub-system being optically disposed to receive electromagnetic radiation from said second optical sub-system;

a positioning sub-system arranged to vary a distance between said two opposing surface;

a data collector interface component operatively connected to said detector and arranged to receive detected data;

at least one processor;

a positioning sub-system interface component arranged to provide positioning information to said positioning sub-system; and, at least one computer readable memory having computer readable code embodied therein, said computer readable code programmed to control said at least one processor to:

receive the detected data from said detector, and vary the distance between said two opposing surfaces to obtain a distance-between the two opposing surfaces that provides a substantially optimum absorbance, wherein the substantially optimum absorbance is the measured absorbance at which the signal-to-noise ratio is maximized;

said data collector interface component, said at least one processor, said positioning sub-system interface component and said at least one computer readable memory being operatively interconnected to one another.

4. The system of claim 3 further comprising:

an electromagnetic radiation source interface component arranged to provide a control signal to said source of electromagnetic radiation;

said electromagnetic radiation source interface component being operatively interconnected with said at least one processor, said positioning sub-system interface component and said at least one computer readable memory.

5. The system of claim 4 wherein said computer readable code is further programmed to control said at least one processor to: obtain an initial absorbance measurement.

6. The system of claim 4 wherein said computer readable code, in varying the distance between the two opposing surfaces, is further capable of causing said at least one processor to:

(a) obtain a measurement at absorbance;

(b) determine whether the measured absorbance is substantially equal to the substantially optimum absorbance;

(c) vary the distance between the two opposing surfaces, if the measured absorbance is not substantially equal to the substantially optimum absorbance;

(d) repeat (a) through (c) until the measured absorbance is substantially equal to the substantially optimum absorbance.

7. The system of claim 3 wherein said first optical sub-system comprises:

a collimating optical sub-system; and an optical delivery sub-system arranged to provide electromagnetic radiation from said source to said collimating optical sub-system;

said collimating optical sub-system being arranged to substantially collimate the provided electromagnetic radiation; and wherein said second optical sub-system comprises:

a receiving optical sub-system arranged to receive electromagnetic radiation transmitted through the sample and said at least a portion of said sample holding assembly; and an optical transmission sub-system arranged to receive electromagnetic radiation from said receiving optical sub-system and transmitting the received electromagnetic radiation to said detecting sub-system.

8. A computer program product comprising:

a computer usable medium having computer readable code embodied therein, the computer readable code programmed to control at least one processor to:

receive detected data from a detector, obtain a measured absorbance, vary a distance between said two opposing surfaces to obtain a distance between the two opposing surfaces wherein the measured absorbance is substantially equal to a substantially optimum absorbance, wherein the substantially optimum absorbance is a measured absorbance at which the signal-to-noise ratio is maximized.

9. The computer program product of claim 8 wherein said computer readable code is further programmed to control the at least one processor to: obtain an initial absorbance measurement.

10. The computer program product of claim 8 wherein said computer readable code, in varying the distance between the two opposing surfaces, is further programmed to control the at least one processor to:

(a) determine whether the measured absorbance is substantially equal to the substantially optimum absorbance;

(b) vary the distance between the two opposing surfaces, if the measured absorbance is not substantially equal to the substantially optimum absorbance;

(c) repeat the obtaining of the measured absorbance;

(d) repeat (a) through (c) if the measured absorbance is not substantially equal to the substantially optimum absorbance.

11. A system comprising:

a source of electromagnetic radiation;

a first optical sub-system;

a sample holding assembly comprising two opposing surfaces spaced apart from each other and arranged to hold a liquid sample;

said first optical sub-system being arranged to provide electromagnetic radiation from said source to said sample holding assembly;

said sample holding assembly being arranged to place the liquid sample in an optical path of the provided electromagnetic radiation; the provided electromagnetic radiation also being transmitted through at least a portion of said sample holding assembly;

a second optical sub-system arranged in receive electromagnetic radiation transmitted through the sample and said at least a portion of said sample holding assembly;

means for detecting electromagnetic radiation;

said second optical sub-system arranged to transmit the received electromagnetic radiation to said detecting sub-system;

said detecting means being optically disposed to receive electromagnetic radiation from said second optical sub-system; and means for varying a distance between said two opposing surfaces until a predetermined distance is obtained that provides a substantially optimum absorbance wherein the substantially optimum absorbance is a measured absorbance at which the signal-to-noise ratio is maximized.

12. A system for measuring absorbance of a small liquid sample, the method comprising:

a sample holding assembly comprising two opposing surfaces spaced apart from each other and arranged to hold a sample;

an optical assembly arranged to detect electromagnetic radiation transmitted through a sample held in the sample holding assembly;

a positioning assembly arranged to vary a distance between said two opposing surface;

at least one processor in data communication with the optical assembly and programmed to determine a measured absorbance of a sample and to control the positioning assembly to vary the distance between said two opposing surfaces to obtain a measured absorbance having a substantially maximized signal-to-noise ratio.

13. The system of claim 1 wherein the at least one processor is programmed to:

determine whether the measured absorbance is substantially equal to a substantially optimum absorbance; and vary the distance between the two opposing surfaces, if the measured absorbance does not have a substantially maximized signal-to-noise ratio.

14. The system of claim 1 wherein the at least one processor is programmed to repeat determining a measured absorbance of a sample, determining whether the measured absorbance is substantially equal to a substantially optimum absorbance, and varying the distance between the two opposing surfaces until the signal-to-noise ratio of the measured absorbance is substantially maximized.

* * * * *